(12) United States Patent
Esser

(10) Patent No.: US 6,221,345 B1
(45) Date of Patent: *Apr. 24, 2001

(54) COSMETIC COMPOSITION

(75) Inventor: Isabelle Claire Helene Marie Esser, Merseyside (GB)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/880,075

(22) Filed: Jun. 20, 1997

(30) Foreign Application Priority Data

| Jun. 20, 1996 | (GB) | 9612945 |
| Dec. 23, 1996 | (GB) | 9626793 |
| Dec. 23, 1996 | (GB) | 9626794 |

(51) Int. Cl.⁷ .................................................. A61K 7/32
(52) U.S. Cl. ............................ 424/65; 424/66; 424/67; 424/68
(58) Field of Search .................... 424/65, 66, 68, 424/67

(56) References Cited

U.S. PATENT DOCUMENTS

| 2,889,253 | * | 6/1956 | Berger et al. | 424/65 |
| 2,893,918 | * | 7/1959 | Abramson | 424/65 |
| 2,962,420 | * | 11/1960 | Rostenberg | 424/65 |
| 3,235,458 | | 2/1966 | Messina . | |
| 3,325,367 | * | 6/1967 | Miechowski | 424/65 |
| 3,553,316 | * | 1/1971 | Rubino | 424/68 |
| 4,673,570 | | 6/1987 | Soldati . | |
| 4,719,103 | | 1/1988 | Krevald et al. . | |
| 5,102,656 | * | 4/1992 | Kasat | 424/66 |
| 5,429,816 | * | 7/1995 | Hofrichter et al. | 424/66 |

FOREIGN PATENT DOCUMENTS

| 19514269 | 10/1996 | (DE) . |
| 19530220 | 2/1997 | (DE) . |
| 0000604 | 2/1979 | (EP) . |
| 0373499 | 6/1990 | (EP) . |
| 95/18598 | 7/1995 | (WO) . |

OTHER PUBLICATIONS

International Search Report Application No. PCT/EP 97/03109 completed Nov. 6, 1997.

Riechstoffe, Aromen, Korperpflegemittel, vol. 23, No. 4, 1973, p. 122 "Aerosol–Antispirant Schaum" (not translated).

Soap/Chemical Specialties, vol. 48, No. 11, 1972, p. 117 "Roll–On Antiperspirant".

* cited by examiner

*Primary Examiner*—Francisco Prats
(74) *Attorney, Agent, or Firm*—Matthew Boxer

(57) ABSTRACT

An antiperspirant or deodorant cosmetic composition suitable for topical application to the human skin, comprising:
   i. an antiperspirant or deodorant active;
   ii. a moisturising cream; and optionally
   iii. a carrier for the antiperspirant or deodorant active.

2 Claims, No Drawings

COSMETIC COMPOSITION

The invention relates to antiperspirant or deodorant compositions, but in particular to antiperspirant compositions, comprising a moisturising cream suitable for topical application to human skin.

The deodorant and antiperspirant market is dominated with products based on aluminium or zirconium salts which are intended to prevent, or at least control, perspiration at the skin surface, particularly on the underarm, whilst often simultaneously providing a perceived degree of deodorancy.

Antiperspirant and deodorant compositions are utilised in many product forms e.g. roll-ons, creams, sticks, aerosols and pump sprays. However all forms suffer from a number of common disadvantages.

A principal disadvantage of many deodorants and antiperspirants is their perceived skin unfriendliness. More particularly, the presence of volatile carriers such as volatile silicones and ethanol, and indeed deodorant and antiperspirant actives is perceived to have a drying and tightening effect on a user's skin following application, resulting in dry skin, reduced skin elasticity and an unpleasant skin sensation.

Many deodorants and antiperspirants can also result in a stinging sensation on the skin following application due to the presence of astringent, skin drying materials such as ethanol. Stinging is a particularly problematic when a deodorant or antiperspirant is applied following shaving.

The above disadvantages deter many consumers from utilising deodorants and antiperspirants thereby depriving the consumer of the benefits to be derived from such cosmetics.

An object of the invention is to provide such a composition which has excellent antiperspirant or deodorant efficacy, excellent cosmetic properties and aesthetics such as comfort in use, smoothness on application, and non-skin drying. The moisturising cream in the composition may also provide moisturising effect.

A further object of the invention is to provide a deodorant or antiperspirant composition which also exhibits reduced stinging upon application, and has low irritation potential. According to the invention there is provided a antiperspirant or deodorant cosmetic composition suitable for topical application to the human skin, comprising:

i. an antiperspirant or deodorant active;
ii. a moisturising cream; and optionally
iii. a carrier for the antiperspirant or deodorant active.

Preferably, an antiperspirant active comprises 5–25% by weight of the composition. Normally the antiperspirant or deodorant composition will additionally comprise a carrier for the antiperspirant or deodorant active, though it is envisaged in certain circumstances, in particular in a cream product formulation, that the composition may comprise a moisturising cream base in which is dissolved or suspended the antiperspirant or deodorant active.

It is a highly preferred aspect of the invention that the composition is an antiperspirant one, in particular one in which the antiperspirant active is based on either aluminium or aluminium/zirconium salts. It has surprisingly been found that moisturizing creams can be combined with antiperspirant actives in topical compositions to provide compositions which are stable.

In certain preferred embodiments, the moisturising cream is a carrier for the active. Also in certain embodiments, the cream can comprise at least 25% by weight of the composition.

In a preferred embodiment, the composition does not contain short chain monohydric alcohols, in particular ethanol, which may be responsible for stinging of the antiperspirant or deodorant compositions, as well as contributing to the drying of the skin.

In another aspect of the invention, there is provided an antiperspirant composition comprising an antiperspirant active, a volatile carrier for the active and a moisturising cream. Also in certain embodiments, the moisturising cream comprises a non-volatile carrier for the antiperspirant carrier.

Advantageously, the composition comprises non-volatile emollients.

In a preferred embodiment, and in particular for cream, roll-on or pump spray product forms, the invention provides an antiperspirant or deodorant composition suitable for topical application to the human skin, comprising:

i. 1–25% by weight of the total composition of an antiperspirant or deodorant active;
ii. 1 to 90% (more preferably 5 to 80%) by weight of the total composition of water; and
iii. 0.1 to 95% (more preferably 5 to 30%) by weight of a moisturising cream.

The moisturising cream component of the compositions according to the invention may comprise an hygroscopic material known as humectant, which may be preferably a polyol or an alcohol, and may be present at a level of 0.1 to 50%, preferably 0.1–30%, more preferably 1 to 30%, most preferably 1.5 to 10% by weight of the total composition.

It is a highly preferred aspect of the invention that the composition comprises water. The composition may conveniently comprise at least 40% water, preferably at least 50% water. Preferably the composition comprises less than 85% water.

Advantageously the moisturising cream comprises a humectant. Humectants are well know in the art, and are cosmetic ingredients intended to increase the water content of the top layers of the skin. This group of ingredients includes primarily hygroscopic agents employed for this specific purpose. Humectants of particular interest for the present invention are polyols and alcohols such as sorbitol, glycerol, ethylene glycol, propylene glycol or mixtures thereof. Preferably, the humectant contains a hydroxyl group.

When the composition does contain water, it is highly preferred that the composition additionally comprises a surfactant and a hydrophobic phase. Additional preferred ingredients include emollients, and optionally volatile silicones. In particular in such compositions, it is preferred that the hydrophobic phase comprises as little as possible of materials which can dry the skin. In particular, the composition may be configured such that it contains a level of volatile silicone which is sufficiently low so as not to cause drying out of the skin.

Surprisingly, we have found that a moisturising cream can be incorporated into an antiperspirant or deodorant cosmetic composition to produce an antiperspirant or deodorant composition which has improved and attractive cosmetic characteristics expected of such compositions as well as excellent efficacy, low irritation potential and non-stinging upon application.

Therefore, the invention provides an antiperspirant or deodorant compositions which exhibit excellent wetness or odour control, but simultaneously contain a cream which moisturises the stratum corneum. This is contrary to what would be expected especially with antiperspirant compositions, where the aim is to prevent moisture loss from the skin.

Preferably, the moisturising cream in the compositions according to the invention can be a solid or a semi-solid emulsion, although the term can equally be applied to non-aqueous products such as wax-solvent based products and ointments. The term also includes dispersion products of cream consistency.

Preferably, the moisturising cream is present in the composition at a level of at least 15%, more preferably greater than 20%, more preferably greater than 25% by weight of the antiperspirant composition.

The moisturising cream component of the composition can be considered as the water, surfactant, hydrophobic phase, and humectant components of the composition, or indeed any components of the antiperspirant composition which are not the antiperspirant active, perfume, preservative, and optional ingredients (e.g. fillers, opacifiers) of the composition The cream in the composition can be of the oil in water type, or water in oil. The cream in the composition should also be stable, and to this end techniques used in the art can be used to stabilize the cream. These include using high shear in preparation, raising the temperature through the phase inversion temperature and appropriately cooling, matching the HLB of the surfactant, and incorporating a lamellar phase.

Moisturising creams used in the compositions according to the invention are those which aid retention of water to plasticise outer layers of the epidermis to promote soft, smooth skin. If water is lost more rapidly from the stratum corneum that it is received from the lower layers of the epidermis, the skin becomes dehydrated and loses its flexibility.

Moisturising creams used in compositions according to the invention may typically work by one or a combination of three main routes, namely occlusion, humectancy and restoration of deficient materials. A given moisturising cream may act by any number of these three preferred routes.

Occlusion consists of reducing the rate of transepidermal water loss through old or damaged skin or in protecting otherwise healthy skin from the effect of a drying environment. The second approach is to use humectants to attract water from the surrounding environment, thereby supplementing the skin's water content. The third approach is to determine the mechanism of the skin moisturisation process, and supplement the skin in its deficiencies.

In compositions according to the invention, it is the moisturising cream component of the composition which provides a moisturising benefit. It is important that the moisturising cream element of the composition provide the moisturisation benefit. Cream compositions can be modified to improve their moisturisation by known techniques, including adding humectants, lipids, hydrophobic ingredients, or other ingredients which counteract any drying effect they may have.

The composition according to the invention comprises an antiperspirant active. Examples of suitable actives include aluminium salts, zirconium salts, aluminium and/or zirconium complexes, for example aluminium halides, aluminium hydroxy halides, zirconyl oxyhalides, zirconyl hydroxyhalides, and mixtures thereof. Specific examples include activated aluminium chlorohydrate, aluminium chlorohydrate, aluminium pentachlorohydrate and aluminium zirconiumchlorohydrate. Useful zirconium salts include zirconium hydroxy-chloride and zirconium oxychloride, Other generally used actives will be known to those skilled in the art. Preferred actives include AAZG (Activated Aluminium Zirconium Glycine), ZAG (Zirconium Aluminium Glycine), and AACH (Activated Aluminium Chorohydrate).

The amount of antiperspirant active present in the composition according to the invention is may be from 5–50% by weight of the composition, preferably from 10–40% by weight, more preferably 20–35% by weight of the composition. Alternatively the antiperspirant active may be present from 1.0 to 35%, preferably 5 to 30%, most preferably 10 to 25% of the total composition.

The deodorant active used in the cosmetics of the invention can be any deodorant active known in the art such as alcohols with the exception of ethanol, antimicrobial actives such as polyhexamethylene biguanides, non-microbiocidal deodorant actives such as triethylcitrate, bactericides and bacteriostatis.

The carrier material for the antiperspirant composition according to the invention can also comprise one or more of volatile carrier fluids, one or more of non-volatile emollients, and one or a combination of thickener and/or structurant materials if required.

The carrier fluid is selected according to the physical form of the cosmetic composition, e.g. volatile low viscosity silicones, low molecular weight hydrocarbons, alcohols with the exception of ethanol, and water, and can be selected by those skilled in the art to provide appropriate physical and sensory properties for the product.

The emollient, if used in the composition, may consist of a single emollient compound or a mixture of emollients, and can typically include fatty acids and fatty alcohol esters, slightly water soluble ethers and alcohols, hydrocarbons, water insoluble ethers, mineral oils and polyorganosiloxanes, and mixtures thereof.

The thickening or structurant agent, when required, is selected according to the product form of the cosmetic composition. It can be any of a number of compositions, including, for example, hydrogenated vegetable oil, hydrogenated castor oil, fatty acids, beeswax, paraffin wax, silicone wax, fatty alcohols, polymers such as hydroxypropylcellulose, clays such as Bentone, natural or synthetic gums, or mixtures or combinations thereof.

The composition according to the invention can optionally comprise other ingredients, in addition to those already identified, depending on the nature and form of the finished product.

Other ingredients can also be included in the compositions of the invention and include surfactants, fillers, fragrances, preservatives and colouring agents for example. These ingredients are selected according to the physical and chemical from of the cosmetic composition.

Surfactants can comprise optionally up to 25%, more commonly up to 5% by weight of the total product, and are particularly useful in formulating emulsion antiperspirant or deodorant compositions, for example for use as pump spray formulations. However for other product types, it is preferred that the composition contains less than about 8% by weight of surfactants. Non-ionic surfactants are particularly preferred.

Fillers can comprise up to about 20%, more commonly up to 10% of the total product and are normally less costly that the essential components of the invention, thereby reducing overall cost. Suitable fillers include aluminium stearate, aluminium tri-stearate, calcium stearate, talc or finely divided polyethylene, an example of which is ACUMIST B18.

Fragrances typically comprise up to about 1% of the total product.

Colouring agents and preservatives can be added as desired.

Other optional ingredients are other cosmetic adjuncts conventionally employed in antiperspirant or deodorant products.

The ingredients which can optionally be present in the composition carrier can conveniently form the balance of the composition.

The composition according to the invention can take any form of a product suited to or adapted for topical application to human skin, and is usually contained in a suitable holder or dispenser to enable it to be applied to the area of the skin, particularly the underarm, where control of perspiration and deodorancy is required. An important ingredient of the cosmetic compositions in the form of a pump-spray, stick and cream is a humectant such as glycerols and sorbitols.

EXAMPLES

Antiperspirant compositions according to the invention have been prepared using methods of manufacturing known in the art.

The invention is further illustrated by the non-limiting following examples.

Example 1

Roll-On Formulation

| CHEMICAL NAME | % Active | % w/w |
| --- | --- | --- |
| Cetyl Alcohol | 100 | 2.00 |
| Cetyl stearyl alcohol | 100 | 3.00 |
| Decyl Ester of Oleic acid | 100 | 2.00 |
| Glyceryl stearate | 100 | 1.50 |
| Blend of fragrance ingredients | 100 | 1.00 |
| Aluminum Chlorhydrate | 50 | 34.5 |
| Water | 100 | 56.00 |
| Total | | 100.00 |

The following test protocol was carried out on the formulation to determine its moisturising abilities of its cream component, which is further described in the context of example 12:

Test Protocol 10 volunteers were chosen. The measured skin sites were on the inner forearms of panellists who had not taken part in any test (involving their arms) for a period of one week previously. Two sites per arm of 20 sq cm were defined by indelible marks, and the products were applied twice a day according to the following protocol. Panellists applied one product ad lib over one site on each arm, the other site having no treatment. Measurements were made on these sites 5 hours later using the Corneometer, which relates to the skin elasticity, followed by the Derma Torque Meter (DTM), which relates to the skin hydration. Panellists re-applied the products after the measurements. Allocation of sites was balanced for left/right and upper/lower application. The test continued for 5 consecutive days.

N.B. Panellists were asked to avoid excessive use of shower gels, soaps etc. on the inner forearms and not to use body creams and moisturisers.

Results

The data below was derived from the analysis of variance. Treatment day was considered as a factor by including data from the previous day in the analysis.

DTM

| FITTED ELASTIC CONSTANT (TORQUE OFF) | | | | | |
| --- | --- | --- | --- | --- | --- |
| Treatment | Day 1 | Day 2 | Day 3 | Day 4 | Day 5 |
| Roll On Cream (Example 1) | 1.905 | 1.958 | 1.901 | 1.819 | 1.752 |
| No Treatment | 1.650 | 1.647 | 1.690 | 1.663 | 1.631 |
| Diff req'd for 95% sig. | 0.200 | 0.148 | 0.144 | 0.124 | 0.107 |
| sig of diff p= | 0.000 | 0.000 | 0.000 | 0.000 | 0.000 |
| No of People | 10 | 10 | 10 | 10 | 10 |

Corneometer

| Treatment | Day 1 | Day 2 | Day 3 | Day 4 | Day 5 |
| --- | --- | --- | --- | --- | --- |
| Roll On Cream (Example 1) | 83.380 | 81.997 | 81.233 | 80.898 | 81.120 |
| No Treatment | 79.236 | 77.228 | 77.380 | 78.335 | 78.369 |
| Diff req'd for 95% sig. | 5.002 | 3.329 | 2.747 | 2.328 | 2.043 |
| sig of diff p= | 0.011 | 0.000 | 0.000 | 0.000 | 0.000 |
| No of People | 10 | 10 | 10 | 10 | 10 |

Conclusion

The following conclusions can be drawn from the studies.

a) The DTM results show that there is significant increase in the elasticity of the skin after one day compared to no treatment.

b) The Corneometer results show that there is a significant increase in the moisturisation of the stratum corneum after two days compared to no treatment.

It can be concluded that the antiperspirant gave significant improvement in the skin elasticity and moisturisation of the stratum corneum.

Example 2

The following cream formulation for an antiperspirant pump was prepared:

| | % Active |
| --- | --- |
| Mixture of glycerine monostearate, fatty alcohol, wax ester and ethoxylated fatty alcohol | 18.00 |
| Cetyl Stearyl Alcohol | 4.00 |
| Dioctyl cyclohexane | 10.00 |
| Dicapryl Ether | 10.00 |
| 2-Phenoxyethanol | 0.40 |
| Glycerin | 8.00 |
| PEG-40 Hydrogenated Castor Oil | 2.00 |
| Water | To 100% |

An identical test protocol to that described in Example 1 was carried out on Example 2.

The following results were obtained:

The data below was derived from the analysis of variance. Treatment day was considered as a factor by including data from the previous day in the analysis.

DTM

FITTED ELASTIC CONSTANT (TORQUE OFF)

| Treatment | Day 1 | Day 2 | Day 3 | Day 4 | Day 5 |
|---|---|---|---|---|---|
| Pump Cream | 2.084 | 2.083 | 2.122 | 2.137 | 2.148 |
| No Treatment | 1.744 | 1.730 | 1.720 | 1.745 | 1.755 |
| Diff req'd for 95% sig. | 0.174 | 0.114 | 0.103 | 0.091 | 0.081 |
| sig of diff p= | 0.000 | 0.000 | 0.000 | 0.000 | 0.000 |
| No of People | 10 | 10 | 10 | 10 | 9 |

Corneometer

| Treatment | Day 1 | Day 2 | Day 3 | Day 4 | Day 5 |
|---|---|---|---|---|---|
| Pump Cream | 96.410 | 96.418 | 95.630 | 96.365 | 96.888 |
| No Treatment | 82.770 | 81.802 | 80.620 | 80.954 | 81.843 |
| Diff req'd for 95% sig. | 3.132 | 2.037 | 2.240 | 1.900 | 1.778 |
| sig of diff p= | 0.000 | 0.000 | 0.000 | 0.000 | 0.000 |
| No of People | 10 | 10 | 10 | 10 | 9 |

Conclusions

The following conclusions can be drawn from the studies.
 a) The DTM results show that there is a significant increase in the elasticity of the skin with Example 2 after one day compared to no treatment.
 b) The Corneomneter results show that there is a significant increases in the moisturisation of the stratum corneum after one day for Example 2 compared to no treatment.

It can be concluded that Example 2 gave a significant improvement in the skin elasticity and moisturisation of the stratum corneum.

The following examples also illustrate compositions of the invention with the moisturising components being defined in a separate column;

Example 3
(Moisturising Cream Suitable for a Stick With and Without Glycerine)

|  | GLYCEROL | NO GLYCEROL |
|---|---|---|
| Stearyl Alcohol | 17.2 | 23.4 |
| Hydrogenated Castorwax Castor Oil | 2.4 | 3.3 |
| PEG-8 distearate | 2.4 | 3.3 |
| Polydecene | 70.0 | 78.0 |
| Glycerine | 8.00 | — |

A suitable complete stick formulation is given in Example 8. The properties of these cream formulations are further described in the context of Example 10.

Example 4
(Moisturising Cream for Use in a Cream AP)

|  | % Active |
|---|---|
| Mineral Oil | 4.00 |
| Cetearyl alcohol | 1.00 |
| Decyl Oleate | 2.00 |
| 2-Phenoxyethanol | 0.40 |
| Cetearyl Alcohol & Polyethylene Glycol Stearate | 5.00 |
| Titanium Dioxide | 0.20 |
| Glycerine | 6.00 |
| Water | to 100% |

A suitable AP cream formulation is given in Example 7. The properties of this cream formulation are further described in the context of Example 9.

Example 5
(Pump Formulation)

|  | Deodorant part % w/w | moisturizing cream % w/w | total formulation % w/w |
|---|---|---|---|
| oil-in water surfactant mixture | — | 5.5 | 5.5 |
| emollient oils | 5.0 | 5.0 | 10.0 |
| PEG 40 hydrogenated castor oil | — | 0.5 | 0.5 |
| antiperspirant active solution | 10.0 | — | 10.0 |
| processing aid | 2.0 | — | 2.0 |
| preservative | — | 0.1 | 0.1 |
| humectant | — | 2.0 | 2.0 |
| perfume | 0.8 | — | 1.0 |
| water | 57.2 | 11.9 | 69.1 |
| total | 75.0 | 25.0 | 100.0 |

A preferred outline pump composition containing moisturising cream comprises 3–7% surfactant, 8–15% emollient oils, 5–15% antiperspirant active, and 60–80% water.

Example 6
(Roll-On Formulation)

|  | Deodorant part % w/w | moisturizing cream % w/w | total formulation % w/w |
|---|---|---|---|
| antiperspirant active solution | 35.0 | — | 35.0 |
| thickener | 1.0 | 1.0 | 2.0 |
| emulsifier mixture | 2.0 | 2.5 | 4.5 |
| emollient oil | — | 1.5 | 1.5 |
| preservative | — | 0.1 | 0.1 |
| perfume | 1.0 | — | 1.0 |
| water | 37.0 | 19.9 | 55.9 |
| total | 75.0 | 25.0 | 100.0 |

A preferred outline roll on lotion composition comprises 30–40% antiperspirant active, 2–8% emulsifier, 0.5–5% emollient oil, and 50–60% water.

Example 7
(AP Cream Formulation)

|  | Deodorant part % w/w | moisturizing cream % w/w | total formulation % w/w |
|---|---|---|---|
| emollient oil | — | 1.0 | 1.0 |
| antiperspirant active solution | 30.0 | — | 30.0 |
| thickener | 0.75 | 0.25 | 1.0 |
| emulsifying agents | 10.75 | 1.75 | 12.5 |
| preservative | — | 0.2 | 0.2 |
| opacifier | 0.2 | — | 0.2 |
| humectant | — | 1.5 | 1.5 |
| perfume | 1.0 | — | 1.0 |
| water | 32.3 | 20.3 | 52.6 |
| total | 75.0 | 25.0 | 100.0 |

A preferred outline cream composition comprises 0.5–5% emollient oil, 25–35% antiperspirant active, 10–15% emulsifier, and 45–60% water.

Example 8
(Stick AP Formulation)

|  | Deodorant part % w/w | moisturizing cream % w/w | total formulation % w/w |
|---|---|---|---|
| carrier oil | 32.0 | — | 32.0 |
| antiperspirant active | 25.0 | — | 25.0 |
| emollient oil | — | 17.5 | 17.5 |
| structuring agent | 10.2 | 4.3 | 14.5 |
| processing aid | 1.4 | 0.6 | 2.0 |
| emulsifying agent | 1.4 | 0.6 | 2.0 |
| skin feel modifier | 4.0 | — | 4.0 |
| perfume | 1.0 | — | 1.0 |
| humectant | — | 2.0 | 2.0 |
| total | 75.0 | 25 | 100.0 |

Comparative experiments as previously described were carried out on Examples 3 to 8.

Results

The data below was derived from the STAVERA1 analysis (analogous to a T test) of variance. Treatment day was considered as a factor by including data from the previous day in the analysis.

Example 9
(With and Without Glycerol)
DTM

FITTED ELASTIC CONSTANT (TORQUE OFF)

| Treatment | Day 1 | Day 2 | Day 3 | Day 4 | Day 5 |
|---|---|---|---|---|---|
| No Glycerol | 2.038 | 2.039 | 2.127 | 2.200 | 2.204 |
| Glycerol | 2.300 | 2.226 | 2.350 | 2.388 | 2.409 |
| No Treatment | 1.895 | 1.925 | 2.039 | 2.049 | 2.093 |
| Diff req'd for 95% sig. | 0.272 | 0.217 | 0.189 | 0.168 | 0.147 |
| sig of diff p= | 0.016 | 0.020 | 0.004 | 0.000 | 0.000 |
| No of People | 8 | 10 | 10 | 10 | 8 |

Corneometer

| Treatment | Day 1 | Day 2 | Day 3 | Day 4 | Day 5 |
|---|---|---|---|---|---|
| No Glycerol | 77.605 | 80.089 | 80.727 | 80.997 | 81.650 |
| Glycerol | 84.532 | 86.801 | 89.393 | 89.920 | 90.328 |
| No Treatment | 74.015 | 76.050 | 77.880 | 78.237 | 79.137 |
| Diff req'd for 95% sig. | 4.064 | 2.920 | 2.764 | 2.534 | 2.257 |
| sig of diff p= | 0.000 | 0.000 | 0.000 | 0.000 | 0.000 |
| No of People | 9 | 10 | 10 | 10 | 10 |

Example 10
(Cream AP)
DTM

FITTED ELASTIC CONSTANT (TORQUE OFF)

| Treatment | Day 1 | Day 2 | Day 3 | Day 4 | Day 5 |
|---|---|---|---|---|---|
| Cream | 2.209 | 2.124 | 2.172 | 2.225 | 2.271 |
| No Treatment | 1.925 | 1.793 | 1.867 | 1.841 | 1.855 |
| Diff req'd for 95% sig. | 0.168 | 0.119 | 0.092 | 0.082 | 0.078 |
| sig of diff p= | 0.002 | 0.000 | 0.000 | 0.000 | 0.000 |
| No of People | 9 | 10 | 10 | 10 | 10 |

Corneometer

| Treatment | Day 1 | Day 2 | Day 3 | Day 4 | Day 5 |
|---|---|---|---|---|---|
| Cream | 93.146 | 93.734 | 94.351 | 95.467 | 96.068 |
| No Treatment | 81.293 | 80.927 | 81.327 | 81.681 | 81.735 |
| Diff req'd for 95% sig. | 4.311 | 3.619 | 2.667 | 2.327 | 2.028 |
| sig of diff p= | 0.000 | 0.000 | 0.000 | 0.000 | 0.000 |
| No of People | 9 | 10 | 10 | 10 | 10 |

In all the examples, moisturisation is deemed only to have occurred if there has been an increase in skin elasticity as measured by the DTM test, and also an increase in skin hydration as measured by the corneometer, relative to an untreated site.

Conclusions

The following conclusions can be drawn from the studies.
Cream of Example 9.
  a) The DTM results show that there is a significant increase in the elasticity of the skin for the cream after one day compared to no treatment.
  b) The Corneometer results show that there is a significant increase in the moisturisation of the stratum corneum after one day for the cream compared to no treatment.

It can be concluded that the "moisturising cream" gives significant improvement in the skin elasticity and moisturisation of the stratum corneum.

Cream of Example 10.

a) The DTM results show that there is a significant increase in the elasticity of the skin after one day for the cream with glycerol compared to no treatment. The cream without glycerol shows an upward trend but this is not significant at the 95% level.

b) The Corneometer results show that there is a significant increase in the hydration of the stratum corneum after one day for the cream with glycerol and after 2 days for the cream without glycerol compared to no treatment.

c) The cream with glycerol is significantly better than the cream without glycerol in increasing the skin elasticity and moisturisation of the stratum corneum after one day.

It can be concluded that the cream containing glycerol provides a moisturising effect as defined, whereas the cream which does not contain the glycerol does not provide a moisturisation effect.

Example 11

The following cream was formulated according to a standard emulsion manufacturing process.

| Component | weight % |
| --- | --- |
| mineral oil | 4.0 |
| cetearyl alcohol | 4.75 |
| glyceryl stearate | 2.0 |
| phenoxyethanol | 0.4 |
| PEG-20 stearate | 1.25 |
| glycerol | 6.0 |
| titanium dioxide | 0.2 |
| water | 81.4 |
|  | 100 |

The above cream was shown to be moisturising in-vivo as it increased the skin elasticity as measured by DIASTRON Dermal Torque Meter, and the skin hydration as measured using a Corneometer CM 820 PC Skin Hygrometer after one day compared to no treatment on a five day test protocol. The increase in skin elasticity and skin hydration versus untreated area were significant at 95% confidence level after one day.

Antiperspirant cream compositions were formulated containing 25% and 50% of the above moisturising cream, and were found to give good cosmetic properties and be very mild on the skin. In this moisturising cream composition, the presence of the humectant (ie glycerol) was found to be very important to the cream's moisturising properties.

Example 12

The following cream was formulated according to the same protocol as described in relation to example 11.

| component | weight % |
| --- | --- |
| ceteareth-20 | 6.0 |
| cetyl alcohol | 4.0 |
| glyceryl stearate | 4.0 |
| decyl oleate | 6.0 |
| water | 80.0 |
|  | 100.0 |

The above cream was shown to be moisturising in-vivo as it increased the skin elasticity as measured by DIASTRON Dermal Torque Meter, and the skin hydration as measured using a Corneometer CM 820 PC Skin Hygrometer after one day compared to no treatment on a five day test protocol. The increase in skin elasticity and skin hydration versus untreated area were significant at 95% confidence level after one day.

An antiperspirant composition suitable for a roll-on applicator was formulated containing 25% of the above moisturising cream and found to give excellent wetness and odour control as well good cosmetic and aesthetic properties such as comfort in use, smoothness on application and non-sting on application.

Example 13

The following creams, which moisturise by occlusion, were formulated according to the following protocol. All ingredients were heated to 75° C. The cream texture was obtained by using a high shear homogeniser as the formulated product is cooling, providing a flowable product.

|  | weight % | | |
| --- | --- | --- | --- |
| component | cream 1 | cream 2 | cream 3 |
| stearyl alcohol | 17.2 | 17.2 | 21.2 |
| PEG-8 distearate | 2.4 | 2.4 | 2.9 |
| hydrogenated castor oil | 2.4 | 2.4 | 2.9 |
| volatile silicone | 78.0 | 68.0 | — |
| polydecene | — | — | 73.0 |
| petroleum jelly | — | 10.0 | — |
| Total | 100.0 | 100.0 | 100.0 |

The moisturising properties of the above creams were determined by measuring the occlusion properties of the creams, i.e the creams are moisturising if they induce a significant reduction in the Trans Epidermal Water Loss (TEWL). An in-vitro TEWL method was used to assess the above creams. The cream needed to reduce the TEWL by a minimum of 15% to be moisturising.

Cream 1 gave a TEWL reduction of 2.5%; cream 2 of 19.4%; and cream 3 of 42.8%.

Cream 1 does not give moisturising benefits, whilst creams 2 & 3 are moisturising.

Antiperspirant compositions suitable for a stick applicator were formulated, one containing 15% of the moisturising cream 2 and one containing 50% of the moisturising cream 3. Both compositions were found to give excellent wetness and odour control as well good cosmetic and aesthetic properties such as comfort in use, smoothness on application and non-sting on application.

What is claimed is:

1. An antiperspirant cream cosmetic composition suitable for topical application to human skin comprising:

(1) an antiperspirant active; and (2) 25 to 50% of the total composition is a moisturizing cream comprising in weight % per 100% moisturizing cream, the amounts of 4% mineral oil, 4.75% cetearyl alcohol, 2.0% glycerol stearate, 0.4% phenoxyethanol, 1.25% PEG-20 stearate, 6% glycerol, 0.2% titanium dioxide and 81.4% water.

2. An antiperspirant roll-on cosmetic composition suitable for topical application to human skin comprising:

(1) an antiperspirant active;
(2) 25% of the total composition is a moisturizing cream comprising in weight % per 100% moisturizing cream, the amounts of 6.0% ceteareth-20, 4% cetyl alcohol, 4% glycerol stearate, 6% decyl oleate and 80% water.

* * * * *